US008066991B2

(12) United States Patent
Jolly

(10) Patent No.: US 8,066,991 B2
(45) Date of Patent: Nov. 29, 2011

(54) ENZYME INHIBITORS OF PAI-1

(75) Inventor: James F. Jolly, Elgin, IL (US)

(73) Assignees: Amano Enzyme USA Co., Ltd., Elgin, IL (US); Amano Enzyme Inc., Nogoya (JP)

( * ) Notice: Subject to any disclaimer, the term of this patent is extended or adjusted under 35 U.S.C. 154(b) by 1446 days.

(21) Appl. No.: 11/545,015

(22) Filed: Oct. 10, 2006

(65) Prior Publication Data

US 2007/0081988 A1  Apr. 12, 2007

Related U.S. Application Data

(60) Provisional application No. 60/724,811, filed on Oct. 11, 2005.

(51) Int. Cl.
| | |
|---|---|
| A61K 38/46 | (2006.01) |
| A61K 38/00 | (2006.01) |
| A61K 35/14 | (2006.01) |
| C12Q 1/37 | (2006.01) |
| C07K 1/00 | (2006.01) |
| C07K 14/00 | (2006.01) |
| C07K 16/00 | (2006.01) |
| C07K 17/00 | (2006.01) |

(52) U.S. Cl. ......... 424/94.65; 514/1.1; 530/380; 435/23
(58) Field of Classification Search .................. None
See application file for complete search history.

(56) References Cited

U.S. PATENT DOCUMENTS

| | | | | | |
|---|---|---|---|---|---|
| 3,860,702 | A | * | 1/1975 | Buell | 424/94.2 |
| 5,328,909 | A | * | 7/1994 | Ando et al. | 514/256 |
| 5,731,328 | A | * | 3/1998 | Berg et al. | 514/324 |
| 2002/0115843 | A1 | * | 8/2002 | Oi et al. | 536/23.2 |
| 2003/0199462 | A1 | * | 10/2003 | Nunez et al. | 514/44 |
| 2005/0158295 | A1 | * | 7/2005 | Swiercz et al. | 424/94.3 |

FOREIGN PATENT DOCUMENTS

| | | |
|---|---|---|
| EP | 1 627 885 A1 | 2/2006 |
| FR | 2 233 038 | 1/1975 |
| WO | WO 95/00169 A | 1/1995 |
| WO | WO 2004/ 096843 A1 | 11/2004 |

OTHER PUBLICATIONS

Andreason et al. "Solvent effects on activity and conformation of plasminogen activator inhibitor-1." Thrombosis and Haemostasis (1999), 81(3), 407-414.*

Urano et al., "The Profibrinolytic Enzyme Subtilisin NAT Purified from *Bacillus subtilis* Cleaves and Inactivates Plasminogen Activator Inhibitor," *The Journ. Of Biol. Chem.*, vol. 276, No. 27, 2001, pp. 24690-24696.

Luisetti et al., "Some Properties of the Alkaline Proteinase from *Aspergillus melleus*," Int. J. Tiss. Reac. XIII(4), 1991, pp. 187-192.

Fossati, "Antiinflammatory Effects of Seaprose-S on Various Inflammation Models," Drugs Exptl. Clin. Res. XXV(6), 1999, pp. 263-270.

Braga et al., "Effects of Seaprose on the Rheology of Bronchial Mucus in Pateints with chronic Bronchitis. A Double-Blind Study vs. Placebo," Int. J. clin. Pharm. Res. XIII(3), 1993, pp. 179-185.

Braga et al., "The Influence of Seaprose on Erythromycin Penetration into Bronchial Mucus in Bronchopulmonary Infections," Drugs Exptl. Clin. Res. XVIII(3), 1992, pp. 105-111.

Moretti et al., "Effects of Seaprose on Sputum Biochemical Components in Chronic Bronchitic Patients: A Double-Blind Study vs. Placebo," Int. J. Clin. Pharm. Res. XIII(5), 1993, pp. 275-280.

Moriya et al., "Intestinal Absorption of Serrapeptase (TSP) in Rats," Biotechnol. Appl. Biochem. 20, 1994, pp. 101-108.

Castell et al., "Intestinal Absorption of Undegraded Proteins in Men: Presence of Bromelain in Plasma After Oral Intake," 1997, pp. 139-146.

Wu et al., "Inhibition of PAI-1: A New Anti-Thrombotic Approach," 2002, pp. 27-42.

Duffy, "Urokinase Plasminogen Activator and Its Inhibitor, PAI-1, as Prognostic Markers in Breast Cancer: from Pilot to level I Evidence Studies," Clinical Chemistry 48:8, 2002, pp. 1194-1197.

Robbie et al., "Inhibitors of Fibrinolysis Are Elevated in Atherosclerotic Plaque," Arteriosclerosis, Thrombosis, and Vascular Biology, vol. 16, No. 4, 1996, pp. 539-545.

Escandon et al., "Amelioration of the inhibition of Fibrinolysis in Elderly, Obese Subjects by Moderate Energy Intake Restriction," Am. J. Clin. Nutr. 1996, pp. 7-11.

Vaughan et al., "Plasminogen Activator Inhibitor-1: A Common Denominator in Cardiovascular Disease," Journal of Investigative Medicine, vol. 46, No. 8, 1998, pp. 370-376.

Sobel et al., "Increased Plasminogen Activator Inhibitor Type 1 in Coronary Artery Atherectomy Specimens from Type 2 Diabetic Compared with Nondiabetic Patients," 1998, pp. 2213-2221.

(Continued)

*Primary Examiner* — Maury Audet
(74) *Attorney, Agent, or Firm* — Foley & Lardner LLP

(57) ABSTRACT

The invention provides a method for the treatment of a subject suffering from a cardiovascular disease using a therapeutically effective amount of at least one enzyme that is capable of inhibiting PAI-1 activity. The invention also provides a method of decreasing the risk of the occurrence of a cardiovascular disease in a subject who presents at least one risk factor that is associated with a cardiovascular disease, by administering to the subject a therapeutically effective amount of at least one enzyme that is capable of inhibiting PAI-1 activity. Additionally, the invention provides a method of inhibiting PAI-1 activity in a subject in need thereof, where the subject is administered an enzyme selected from a protease or peptidase.

8 Claims, 10 Drawing Sheets

OTHER PUBLICATIONS

Pandolfi et al., Plasminogen Activator Inhibitor Type 1 is Increased in the Arterial wall of Type II Diabetic Subjects, Arteriosclerosis, Thrombosis, and Vascular Biology, 2001, pp. 1378-1382.

Mertens et al., "Visceral Fat as a Determinant of Fibrinolysis and Hemostasis," Seminars in Vascular Medicine, vol. 5, No. 1, 2005, pp. 48-55.

Hamsten et al., "Plasminogen Activator Inhibitor in Plasma: Risk Factor for Recurrent Myocardial Infarction," The Lancet, 1987, pp. 3-9.

Lijnen, Pleitropic Functions of Plasminogen Activator Inhibotor-1, Journ. Of Thrombosis and Haemostasis, 3: 2004, pp. 35-45.

Yamamoto, "Aging and Plasminogen Activator Inhibitor-1 (PAI-1) regulation: implication in the Pathogenesis of Thrombotic Disorders in the Elderly," Cardiovascular Research 66, 2005, pp. 276-285.

Taeye, et al., "Plasminogen Activator Inhibitor-1: A Common Denominator in Obesity, Diabetes and Cardiovascular Disease," 2005, pp. 149-154.

Festa et al., Elevated Levels of Acute-Phase Proteins and Plasminogen Activator Inhibitor-1 Predict the Development of Type 2 Diabetes, 2002, pp. 1131-1137.

Ye et al., Synthesis and Biological Evaluation of Piperazine-Based Derivatives as Inhibitors of Plasminogen Activator Inibitor-1 (PAI-1), 2004, pp. 761-765.

Friederich et al., "Novel Low-Molecular-Weight Inhibitor of PAI-1 (XR5118) Promotes Endogenous Fibrinolysis and Reduces Post-thrombolysis Thrombus Growth in Rabbits," 1997, pp. 916-921.

Berry et al., "Antithrombotic Activity of a Monoclonal Antibody Inducing the Substrate Form of Plasminogen Activator Inhibitor Type 1 in Rat Models of Venous and Arterial Thrombosis," 1998, pp. 29-34.

Giezen et al., "The Fab-Fragment of a PAI-1 Inhibiting Antibody Reduces Thrombus Size and Restores Blood Flow in a Rat Model of Arterial Thrombosis," 1997, pp. 964-969.

Fay, et al., "Human Plasminogen Activator Inhibitor-1 (PAI-1) Deficiency: Characterization of a Large Kindred With a Null Mutation in the PAI-1 Gene," 1997, pp. 204-208.

Crandall et al., "Characterization and Comparative Evaluation of a Structurally Unique PAI-1 Inhibitor Exhibiting Oral In-Vivo Efficacy," 2004, pp. 1422-1428.

Biemond et al., Thrombolysis and Reocclusion in Experimental Jugular Vein and Coronary Artery Thrombosis, 1995, pp. 1175-1181.

Carmeliet et al., "Plasminogen Activator Inhibitor-1 Gene-Deficient Mice: II. Effects on Hemostasis, Thrombosis, and Thrombolysis," The Journ. Of Clin. Invest., vol. 92(6), 1993, pp. 1-12.

Elokdah et al., Tiplaxtinin, A Novel, Orally Efficacious Inhibitor of Plasminogen Activator Inhibitor-1: Design, Synthesis, and Preclinical Characterization, 2004, pp. 3491-3494.

Levi et al., Inhibition of Plasminogen Activator Inhibotor-1 Activity Results in Promotion of Endogenous Thrombolysis and inhibition of Thrombus Extension in Models of Experimental Thrombosis, 1992, pp. 305-312.

Liang et al., Characterization of a Small Molecule PAI-1 Inhibitor, ZK4044, 2005, pp. 341-350.

Sumi, H., et al., "Enhancement of the fibrinolytic activity in plasma by oral administration of nattokinase," Copyright 1998 Elsevier Science B.V. Amsterdam, 1990 EMB-1990367850, Acta Haematologica, pp. 139-143, vol. 84, No. 3, abstract, [XP-002441112].

"Novel digestive organ absorptive polypeptide, useful for detecting toxicity of test substance in living organism, treating glucose tolerance disorder, type II diabetes, for manufacturing ice cream, soft drink, fruit drink," Derwent Publications Ltd., London, 2004-804720, 2004, abstract [XP-002441290].

Metzig, C., et al., "Bromelain proteases reduce human platelet aggregation in vitro, adhesion to bovine endothelial cells and thrombus formation in rat vessels in vivo," Biosciences Information Service, 1999, pp. 7-12, vol. 13, No. 1, abstract [XP-00244118].

Gutfreund A.E., et al., "Effect of oral bromelain on blood pressure and heart rate of hypertensive patients," Copyright 1998 Elsevier Science B.V., Amsterdam, 1978, pp. 143-146, vol. 37, No. 5, abstract [XP-002441120].

Hofbauer, R., "Modern aspects of bromelain: A brief review," Copyright 2003 Elsevier Sceince B.V., Amsterdam, 2002, pp. 50-55, vol. 3, No. 3, abstract [XP-002441119].

Meletis, C., "Cardivascular Disease Phytochemical and Nutritional Prevention and Treatment," Alternative & Complementary Therapies, 2003, pp. 158-162, vol. 9, No. 4 [XP-00931805].

Gaciong, Z., et al., "Beneficial effect of proteases on allograft arteriosclerosis in a rat aortic model," Nephrology Dialysis Transplanatation, 1996, pp. 987-989, vol. 11 [XP-002082013].

Bracale, G., et al., "[Clinical study of the efficacy of and tolerance to seaprose S in inflammatory venous disease. Controlled study versus serration-peptidase]," U.S. National Library of Medicine, 1996, pp. 515-524, vol. 44, No. 10 abstract [XP-002441121].

Urano, T., et al., "The Profibrinolytic Enzyme Subtilisin NAT Purified form *Bacillus subtilis* Cleaves and Inactivates Plasminogen Activator Inhibitor Type 1*," The Journal of Biological Chemistry, 2001, pp. 24690-24696, vol. 276, No. 27, [XP-009067066].

Andreasen, P.A., et al., "Solvent Effects on Activity and Conformation of Plasminogen Activator Inhibitor-1," Thrombosis and Haemostasis, 1999, pp. 407-414, vol. 81, No. 3 [XP-002441114].

Kjøller, L., et al., "Conformational changes of the reactive-centre loop and β-strand 5A accompany temperature-dependant inhibitor-substrate transition of plasminogen-activator inhibitor-1," Eur. J. Biochem., 1996, pp. 38-46, vol. 241, No. 1 [XP-002441115].

Pedersen, K., et al., "Plasminogen activator inhibitor-1 polymers, induced by inactivating amphipathic organochemical ligands," Biochem. J., 2003, pp. 747-755, vol. 372, No. 3 [XP-002441113].

Anonymous, "MRM SerraTrol, Serrapeptidase to support healthy circulation," URL:http://store.1-bb.net/product_info.php, 2006, p. 1 abstract [XP-002441116].

Basila, D., et al., "Effects of dietary supplements on coagulation and platelet function," Thrombosis Research, 2005, pp. 49-53, vol. 117, No. 1-2 [EP-005150699].

International Search Report, Jul. 19, 2007.

International Preliminary Report on Patentability, issued on Apr. 16, 2008, in application No. PCT/US2006/039415.

* cited by examiner

Inhibition of PAI-1 with Bromelain

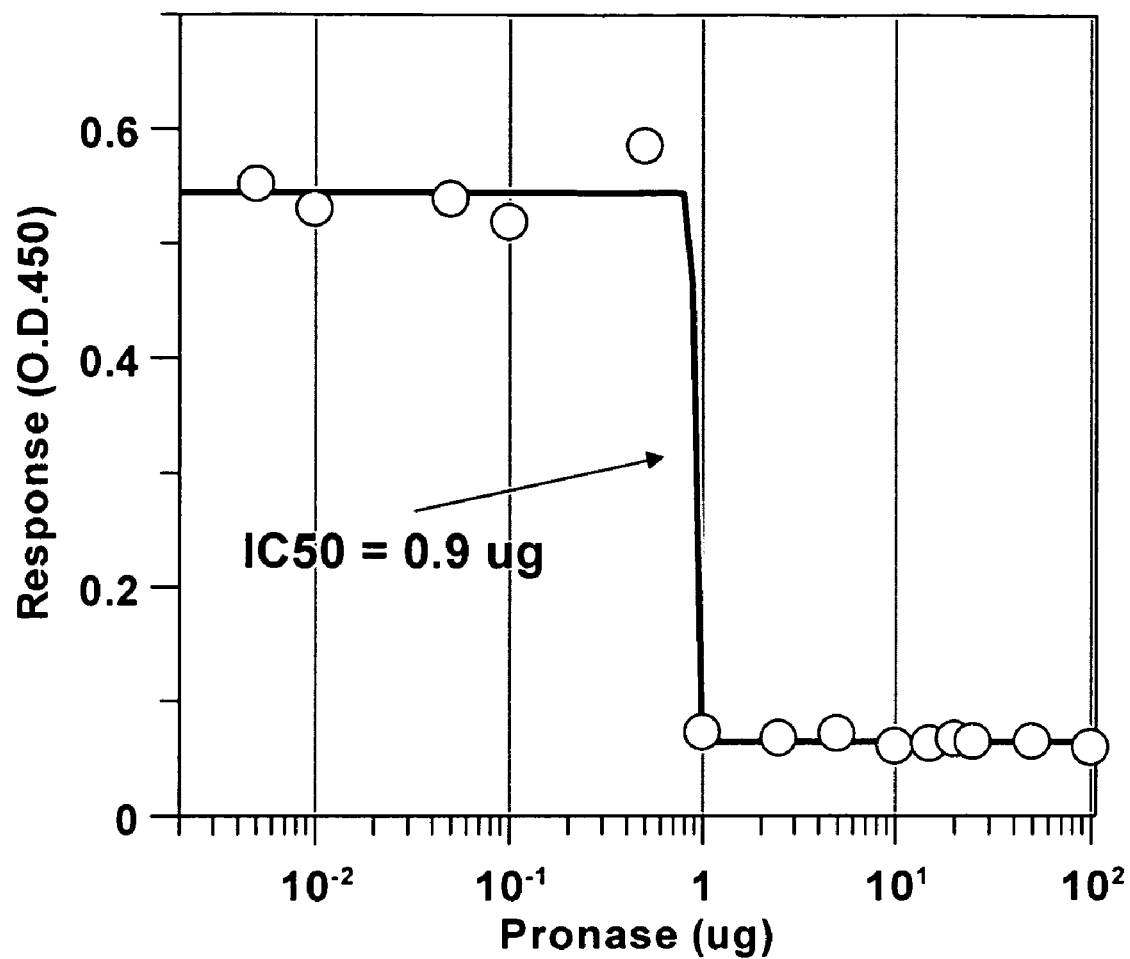

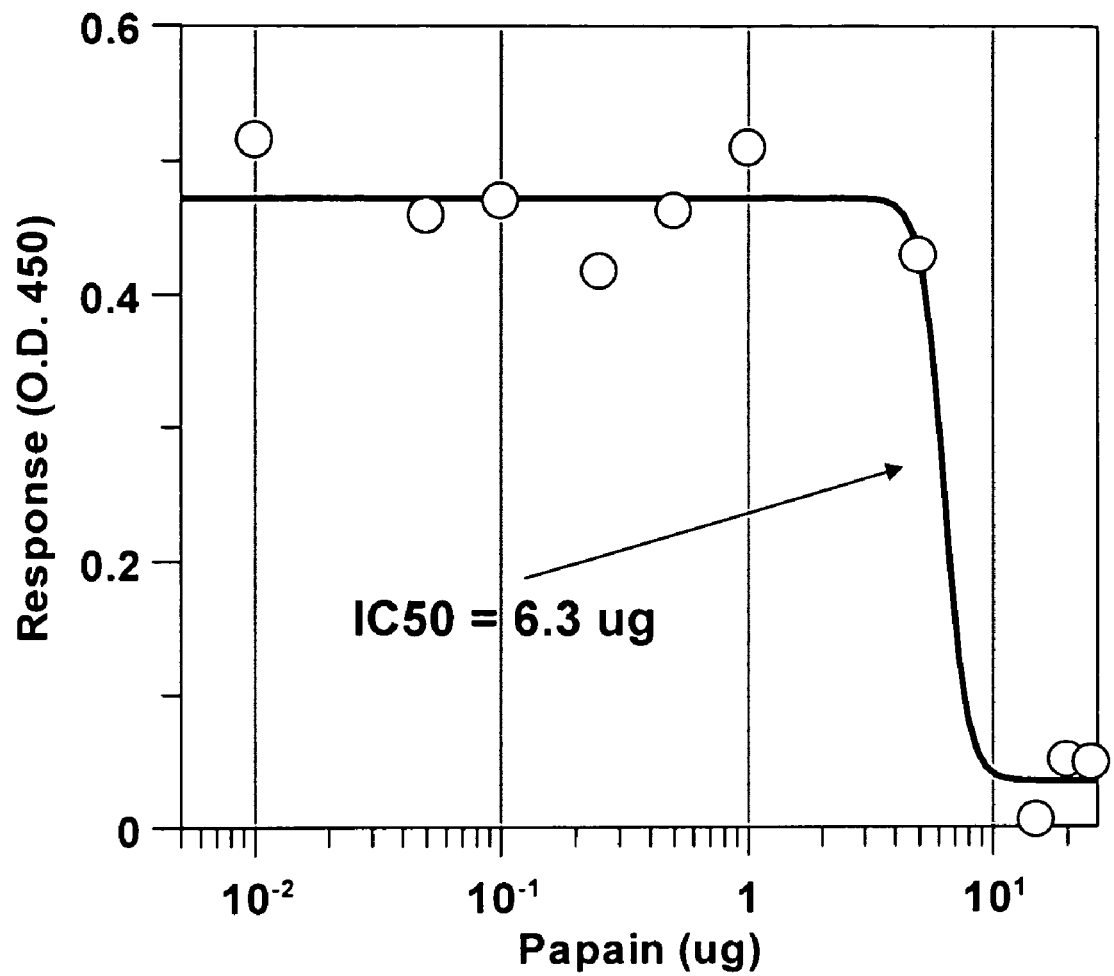

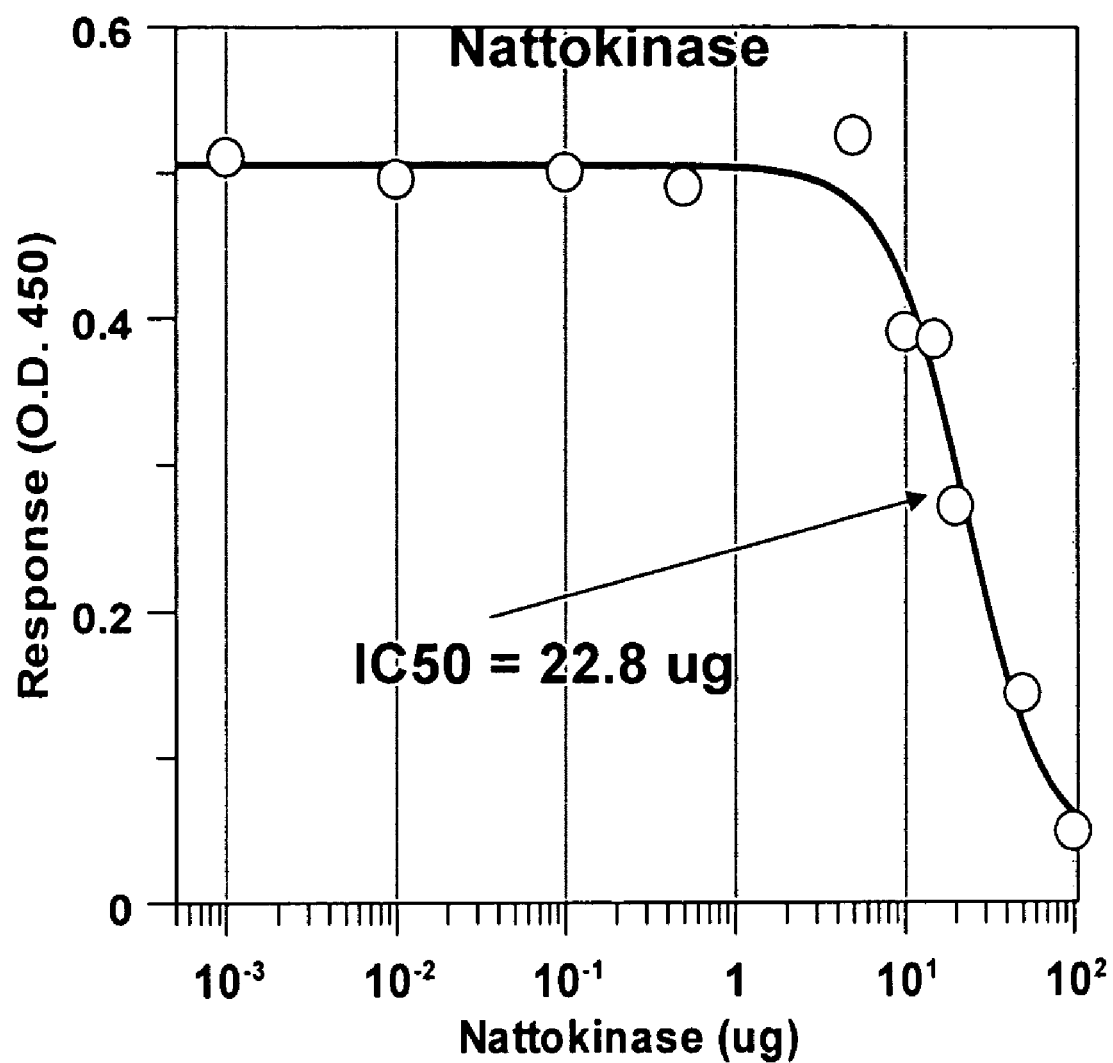

US 8,066,991 B2

ENZYME INHIBITORS OF PAI-1

This application claims the benefit of priority from U.S. Provisional Patent Application No. 60/724,811, which was filed on Oct. 11, 2005.

BACKGROUND OF THE INVENTION

Plasminogen activator inhibitor type 1 (PAI-1) is the major negative regulator of tissue-type plasminogen activator (tPA-1) and urokinase (uPA) in the fibrinolytic system (Q. Wu et al., *Current Drug Targets—Cardiovascular & Haematological Disorders* 2 (2002) 27-42). High levels of PAI-1 reduce fibrinolytic potential and can therefore contribute to the development of thrombosis. Thrombotic cardiovascular diseases are particularly evident in elderly populations, but they are also induced in a variety of pathologies associated with aging in general, such as obesity, insulin resistance, diabetes, emotional stress, immune responses, vascular sclerosis or remodeling, and cardiovascular disease generally (K. Yamamoto et al., *Cardiovascular Research* 66 (2005) 276-285; B. De Taeye et al., *Current Opinion in Pharmacology* 5 (2005) 149-154).

A number of PAI-1 inhibitors have been reported recently. These include small molecules, antibodies, and peptides (B. Ye et al., *Bioorganic & Medicinal Chemistry Letters* 14 (2004) 761-765; A. Liang et al., *Thrombosis Research* 115 (2005) 341-350; C. N. Berry et al., *British Journal of Pharmacology* 125 (1998) 20-34; J. J. J. van Giezen et al., *Thrombosis and Haemostasis* 77 (1997) 964-969; P. R. Guzzo et al., *Tetrahedron Letters* 43 (2002) 41-43).

Despite the clear therapeutic potential of inhibiting PAI-1, enzymes that are capable of achieving this activity in vivo have not heretofore been identified. Subtilisin NAT (nattokinase) was shown recently to cleave PAI-1 in vitro, presumably by virtue of the enzyme's proteolytic activity, but a similar in vivo activity has not been reported (T. Urano et al., *Journal of Biological Chemistry* 276 (2001) 24690-24696).

There is a need, therefore, for enzymes that can be used in vivo to inhibit PAI-1.

SUMMARY OF THE INVENTION

In accordance with one embodiment, the invention provides a method of inhibiting PAI-1 activity in a subject in need thereof. The method comprises administering to the subject an enzyme selected from a protease or peptidase.

In accordance with another embodiment, the invention provides a method for the treatment of a subject suffering from a cardiovascular disease. The method comprises administering to the subject a therapeutically effective amount of at least one enzyme that is capable of inhibiting PAI-1 activity.

In accordance with another embodiment, the invention provides a method of decreasing the risk of the occurrence of a cardiovascular disease in a subject. The method comprises administering to a subject who presents at least one risk factor that is associated with a cardiovascular disease, a therapeutically effective amount of at least one enzyme that is exhibits PAI-1 inhibiting activity.

The invention also provides a use of at least one enzyme that is capable of inhibiting PAI-1 activity in the manufacture of a medicament for the treatment of a subject suffering from a cardiovascular disease.

In accordance with another embodiment, the invention provides a use of at least one enzyme that is capable of inhibiting PAI-1 activity in the manufacture of a medicament for administration to a subject for decreasing the risk of the occurrence of a cardiovascular disease in the subject, wherein the subject presents at least one risk factor that is associated with a cardiovascular disease.

In accordance with another embodiment, the invention provides a use of an enzyme selected from a protease or peptidase in the manufacture of a medicament for administration to a subject for inhibiting PAI-1 activity in the subject.

BRIEF DESCRIPTION OF THE DRAWINGS

FIG. 8 charts the extent of PAI-1 inhibition as a function of the concentration of pronase in human serum.

FIG. 9 charts the extent of PAI-1 inhibition as a function of the concentration of papain in human serum.

FIG. 10 charts the extent of PAI-1 inhibition as a function of the concentration of nattokinase in human serum.

DETAILED DESCRIPTION

Figure 1:
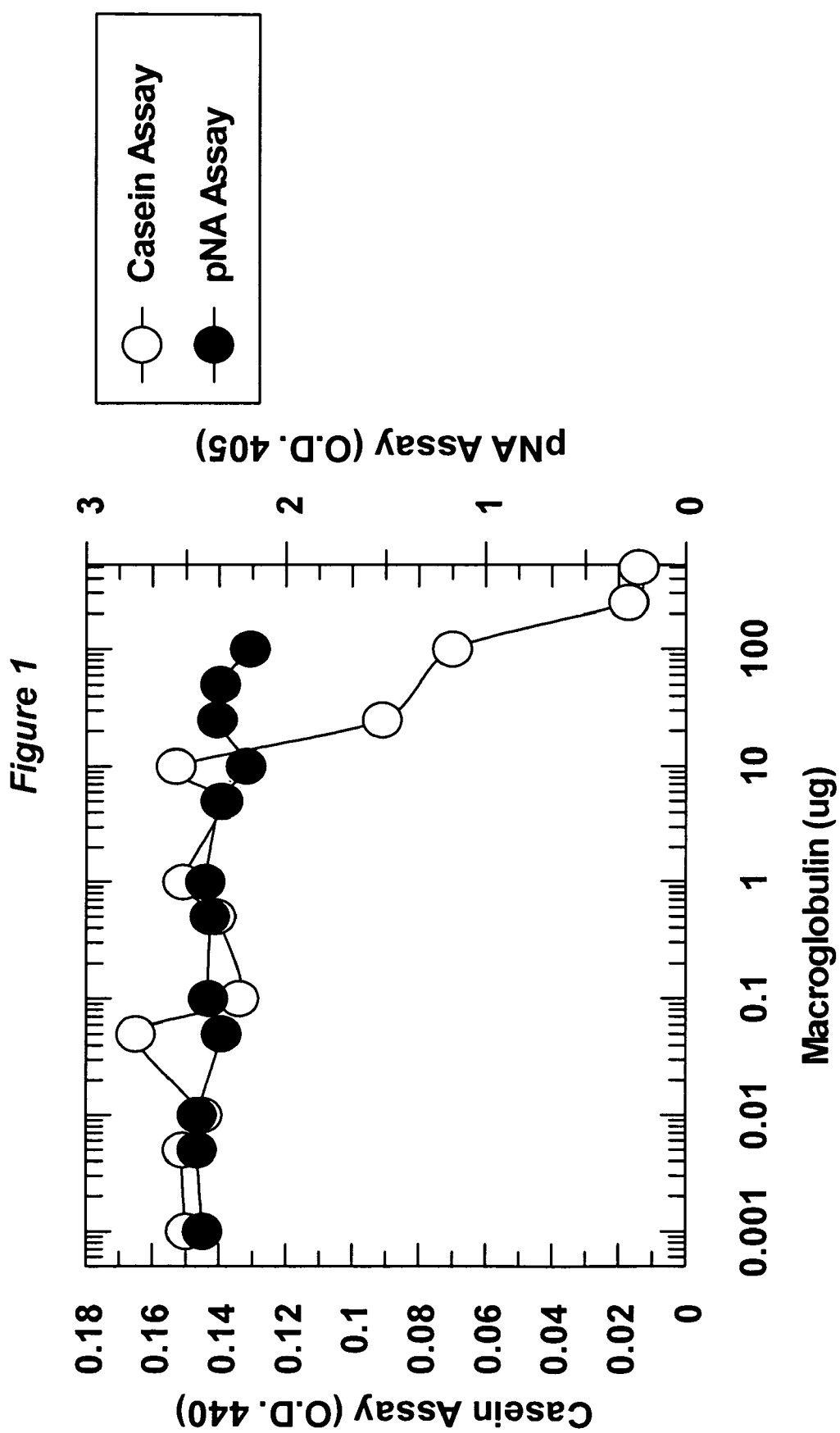
FIG. 1 charts the inhibition of Seaprose protease activity, but not peptidase activity, by macroglobulin.

As used herein, the words "a," "an," and "the" mean "one or more," unless otherwise specified. In addition, where aspects of the invention are described with reference to lists of alternatives, the invention includes any individual member or subgroup of the list of alternatives and any combinations of one or more thereof.

The present inventor discovered that a protease or peptidase inhibits PAI-1 activity, and does so at concentrations that are appropriate for in vivo uses. The inventive methods described herein are useful in treating cardiovascular diseases, as well as decreasing the risk of such diseases occurring in subjects who present risk factors for the diseases. The enzymes described herein are known to be safe for consumption by animals, including humans, and have been used for purposes not related to their newly discovered PAI-1 activity.

The enzymes described herein exhibit PAI-1 inhibiting activity in vivo. Thus, one embodiment of the invention provides a method of inhibiting PAI-1 activity in vivo in a subject in need thereof by administering to the subject an enzyme selected from a protease or peptidase in an amount that is effective to inhibit PAI-1 activity, i.e., a therapeutically effective amount.

In one embodiment, the enzyme is a protease. Illustrative proteases include but are not limited to semi-alkaline protease, bromelain, serapeptase, pronase, and papain. These proteases have long been recognized to exhibit anti-inflammatory and fibrinolytic properties. Thus, known indications for such proteases include, for example, inflammation from sports injuries, mucosal buildup in the sinuses, and lung diseases. The heretofore known indications, however, do not include any conditions related to elevated levels of PAI-1 activity. Proteases and peptidases such as those listed above are conveniently available from commercial sources or they can be obtained and isolated in various purities using well known procedures in the art. Other suitable enzymes that exhibit PAI-1 inhibiting activity can be identified, for example, using the enzyme activity assays described in the examples.

In some embodiments, alone or in combination with any other embodiment herein described, the enzyme is not nattokinase.

Another embodiment of the invention provides a method of treating a subject suffering from a cardiovascular disease, comprising administering to the subject a therapeutically effective amount of at least one enzyme that exhibits PAI-1 inhibiting activity. In one embodiment, the enzyme is a protease or peptidase. In another embodiment, the enzyme is one of the proteases listed above. For example, the enzyme can be semi-alkaline protease or bromelain.

The cardiovascular disease that can be treated or prevented in accordance with the invention is not limited to any particular disorder. Exemplary diseases in this regard include but are not limited to ischemic heart disease, arteriosclerosis, atherosclerosis, hypertension, angina, heart attack, stroke, deep vein thrombosis, disseminated intravascular coagulation, premature myocardial infarction, and coronary artery disease.

The invention additionally contemplates a method of decreasing the risk of occurrence of a cardiovascular disease in a subject. Suitable subjects may present at least one risk factor that is associated with a cardiovascular disease. The subject is administered a therapeutically effective amount of at least one enzyme that exhibits PAI-1 inhibiting activity. Any of the enzymes described above are suitable for use in this method. For example, the enzyme can be a protease such as semi-alkaline protease or bromelain.

Risk factors associated with cardiovascular disease are well known, and thus afford the clinician a means by which to identify that patient population for which prevention of cardiovascular disease is warranted. Such risk factors include, but are not limited to, obesity, diabetes, high blood pressure, stress, lowered estrogen levels, chronic inflammation, and combinations thereof. Subjects who present with more than one risk factor may be that much more susceptible to developing cardiovascular disease, and are appropriate subjects for the preventative treatment as provided by the invention.

In accordance with the invention, the enzymes can be administered alone or in combination with each other, or with other active or inactive agents. When combinations of enzymes are used, the invention contemplates simultaneous or sequential administration of at least two different enzymes.

While the enzymes can be administered in their essentially pure forms, it may be desirable to formulate the enzymes into compositions prior to administration in order to increase, for example, enzyme palatability, subject compliance with a treatment regimen, and/or general ease of administration. Thus, the invention encompasses the use of enzyme compositions that comprise other components in addition to one or more enzymes with PAI-1 inhibitory activity, such as one or more pharmaceutically acceptable binding agents, lubricating agents, suspending agents, sweeteners, flavoring agents, preservatives, buffers, wetting agents, disintegrants, effervescent agents, and other excipients. Such excipients are known in the art and can be readily selected by the skilled artisan.

In one embodiment, the enzyme composition is blended with at least one pharmaceutically acceptable excipient, diluted by an excipient or enclosed within a carrier that can be in the form of a capsule, sachet, tablet, buccal, lozenge, paper, or other container. When the excipient serves as a diluent, it may be a solid, semi-solid, or liquid material which acts as a vehicle, carrier, or medium for the balance of the composition. Thus, the composition can be formulated into tablets, pills, powders, elixirs, suspensions, emulsions, syrups, capsules (such as, for example, soft and hard gelatin capsules), suppositories, lozenges, buccal dosage forms, sterile injectable solutions, and sterile packaged powders.

Examples of binding agents include various celluloses and cross-linked polyvinylpyrrolidone, microcrystalline cellulose, such as Avicel PH101 and Avicel PH102, microcrystalline cellulose, silicidized microcrystalline cellulose (SMCC), and mannitol.

Suitable lubricants, including agents that act on the flowability of the powder formulation to be compressed, include colloidal silicon dioxide, such as Aerosil 200; talc, stearic acid, magnesium stearate, calcium stearate, and silica gel.

Examples of sweeteners include natural or artificial sweeteners, such as sucrose, xylitol, sodium saccharin, cyclamate, aspartame, and acesulfame and salts thereof. Examples of flavoring agents are Magnasweet (trademark of MAFCO), bubble gum flavor, fruit flavors, and the like.

Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, dibasic calcium phosphate, saccharides, and/or mixtures of any of the foregoing. Examples of diluents include microcrystalline cellulose, such as Avicel PH101 and Avicel PH102; dibasic calcium phosphate such as Emcompress; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents include effervescent couples, such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the acid component of the effervescent couple may be present.

In some embodiments of the invention, the enzyme composition is formed into dosage units suitable for oral administration. For example, the one or more enzymes that inhibit PAI-1 activity can be mixed with a solid, pulverant carrier such as, for example, sorbitol, mannitol, starch, amylopectin, cellulose derivatives or gelatin, as well as with an antifriction agent such as, for example, magnesium stearate, calcium stearate, and polyethylene glycol waxes. The mixture then can be pressed into tablets. If coated tablets are desired, the above prepared tablets may be coated, such as with a concentrated solution of sugar, which may contain gum arabic, gelatin, talc, titanium dioxide, or with a lacquer dissolved in volatile organic solvent or mixture of solvents. To this coating, various dyes can be added in order to distinguish among tablets with different enzymes or with different amounts of an enzyme present.

The invention also contemplates providing the one or more enzymes in soft capsules suitable for oral administration, such as capsules which contain a mixture of the one or more enzymes with vegetable oil or non-aqueous, water miscible materials such as, for example, polyethylene glycol and the like. Alternatively, the enzyme(s) can be provided in hard capsules that can contain granules of the enzyme composition in combination with a solid, pulverant carrier, such as, for example, sorbitol, mannitol, potato starch, corn starch, amylopectin, cellulose derivatives, or gelatin.

Dosage units for rectal administration also are contemplated. These can be prepared in the form of suppositories which contain the enzyme(s) and a neutral fat base. Alternatively, they can be prepared in the form of gelatin-rectal capsules which contain the enzyme(s) in a mixture with a vegetable oil or paraffin oil.

Other embodiments include granulated forms of the enzyme compositions described herein. Granulated forms are useful for preparing tablets for oral use, and are typically prepared in the following manner, although other techniques well known in the art can be employed. The solid substances (including the one or more enzymes) are gently ground or sieved to a desired particle size, and the resulting mass is gently pressed through a stainless steel sieve having a desired size. The layers of the mixture are then dried in controlled drying units for a determined length of time to achieve a desired particle size and consistency. The granules of the dried mixture are gently sieved to remove any powder. To this mixture can be added optional disintegrating, anti-friction, and/or anti-adhesive agents. Finally, the mixture is pressed into tablets using a machine with the appropriate punches and dies to obtain the desired tablet size. The operating parameters of the machine can be selected by the skilled artisan.

Lozenge and buccal dosage forms comprising the one or more enzymes with PAI-1 inhibitory activity also are useful in the invention; These can be prepared by methods known to one of ordinary skill in the art.

The one or more enzymes of the present invention also can be formulated in compositions that release the enzyme over an extended period of time, such as, for example, between about two to about sixteen hours. In some embodiments, the enzyme is released over a time of between about three to about twelve hours. In yet other embodiments, the enzyme is released over a time of between about four to about eight hours. Those who are skilled in the art can prepare such sustained release formulation by methods that are known in the art.

In other embodiments, the enzyme(s) may be present in a core surrounded by one or more layers including, for example, an enteric coating layer with or without a protective sub-coating as known to the ordinarily skilled artisan relative to pharmaceutical formulations. If no sub-coating is employed, then the enteric coating can be selected such that it does not degrade the active ingredient in the core.

The enteric layer typically comprises a polymer with enteric properties. Exemplary enteric polymers include, but are not limited to, methacrylic acid copolymer, hydroxypropyl methylcellulose phtalate and hydroxypropyl methylcellulose acetate succinate. Different types of methacrylic acid copolymers can be used, such as, for example, methacrylic acid copolymer type A (Eudragit® L-100), methacrylic acid copolymer type B (Eudragit® S-100), methacrylic acid copolymer type C (Eudragit® L 30D55, Eudragit® L-100-55), a copolymer of methacrylic acid methyl methacrylate and methyl methacrylate (Eudragit®. FS) and mixtures thereof, for instance, a mixture of Eudragit® L-100-55 and Eudragit® S-100 at a weight ratio of about 3:1 to about 2:1, or a mixture of Eudragit® L 30D55 and Eudragit® FS at a weight ratio of about 3:1 to about 5:1.

The enteric layer may further comprise other agents such as cellulose acetate phthalate, polyvinyl acetate phthalate, cellulose acetate trimellitate, shellac and/or zein.

Optionally, the enteric layer further comprises anti-tackiness agents such as talc or glyceryl monostearate; plasticizers such as triethylcitrate or polyethylene glycol; and/or pigments such as titanium dioxide or ferric oxides.

The enteric layer may further comprise one or more plasticizers including, but not limited to, acetyl triethyl citrate, acetyltributyl citrate, acetylated monoglycerides, glycerin, triacetin, propylene glycol, phthalate esters (e.g., diethyl phthalate, dibutyl phthalate), castor oil, sorbitol and dibutyl seccate.

In one embodiment, the invention provides for an enterically coated formulation where the enteric layer comprises hydroxypropyl methylcellulose phthalate, triacetin, silica and stearic acid.

As used herein, the phrase "a therapetucially effective amount" connotes an amount effective to inhibit PAI-1 activity in the subject. This amount may vary from subject to subject, and may generally range from about 20 to about 40 mg per day. In another embodiment, the dosages range from about 25 to about 35 mg per day. An exemplary dosage is about 30 mg per day. A therapeutically effective amount of an enzyme composition of the invention can be administered once daily. Alternatively, a therapeutically effective amount can be administered in divided amounts multiple times per day. An illustrative dosing regimen is about 15 mg of the enzyme composition given twice per day. Alternate suitable dosages can be determined by the skilled artisan.

The following examples are given to illustrate the present invention. It should be understood, however, that the invention is not to be limited to the specific conditions or details described in these examples.

EXAMPLE 1

Inhibition of PAI-1 by Various Enzymes

The purpose of this example was to evaluate the extent to which various enzymes inhibit PAI-1, and to determine therefore the efficacy of each enzyme in treating a cardiovascular disease.

Semi-alkaline protease ("Seaprose"), nattokinase, bromelain and papain were obtained from Amano Enzyme USA Co., Ltd. Serapeptidase was extracted from Dasen 10 mg tablets (Takeda) with water. Fibrinogen, thrombin, $\alpha_1$-antitrypsin ("AAT"), $\alpha_1$-antichymotrypsin ("ACT"), $\alpha_2$-macroglobulin ("MG") and azocasein were obtained from Sigma Chemical Co.

Inhibition studies with AAT, ACT and MG (0-100 µg) were carried out with 1 µg of protease in 100 µl of water at 37° C. for 1 hour. Protease activity for each enzyme was then measured by the addition of 100 µl of 10 mg/mL azocasein and incubating for 1 hour at 37° C. To stop the protease reaction, 200 µl of 10% trichloroacetic acid ("TCA") was added. The reaction mixtures were then vortexed and centrifuged at 10,000 RPM for 10 minutes in a micro centrifuge. The O.D.$^{440}$ of the supernatant was determined as a measure of protease activity. In Table 1 below, the symbol "−" indicates that no inhibition was observed at any concentration of inhibitor used, while "+" indicates that 100% inhibition was observed.

PAI-1 inhibition studies for each protease enzyme were performed by incubating 0-100 µg of a protease with 100 µl of human plasma (Innovative Research, Inc.) for 1 hour at 37° C. The PAI-1 activity in the plasma was then determined by ELISA assay (Innovative Research, Inc.). $IC_{50}$ values were determined by a kinetic software package (GraFit Version 5, Erithacus Software Ltd., Horley, U.K.). The $IC_{50}$ refers to the amount of an enzyme required for inhibition of 50% of PAI-1 activity in 0.1 ml of human plasma. Table 1 below summarizes these values for each enzyme.

Kinetic experiments to perform enzyme activity assays employed the Fibrinolytic Unit assay (FU). Thus, a test tube containing 1.4 mL of 50 mM sodium borate (pH 8.5) and 0.4 ml of 0.72% fibrinogen was pre-incubated at 37° C. for 5 minutes. Then, 0.1 mL of thrombin solution (200 U/ml in 50 mM sodium borate buffer) was added and the tube contents were mixed. After 10 minutes 0.1 mL of a protease was added and the resultant solution was further incubated at 37° C. After 60 minutes of incubation with the protease, 2 mL of 0.2M TCA was added, and the tube contents were mixed and further incubated at 37° C. for 20 minutes. A 1 mL aliquot of the reaction mixture was transferred to a centrifuge tube and centrifuged in a micro centrifuge at 15,000 RPM for 5 minutes. The $O.D.^{275}$ of the supernatant solution was determined.

One unit of activity is the amount of protease that will increase the $O.D.^{275}$ by 0.01/min under the reaction conditions. Km studies were carried out with the FU assay but by varying the fibrinogen concentration from 0-10 mM. The Km values were determined by the GraFit kinetic software package. As used herein, the term Km refers to the Michaelis constant which refers to the concentration of substrate that corresponds to half maximal enzymatic activity when the activity is measured as a function of substrate concentration. In this context, it is a measure of the affinity of an enzyme for substrate. Thus, a low Km characterizes an enzyme that has a high affinity for the substrate, which is preferable since a high affinity for substrate usually means a more efficient enzyme. As used in Table 1 below, specific activity refers to the units of enzyme activity in the fibrinolytic unit (FU) assay per gram of enzyme. Additionally, catalytic efficiency was calculated by using the formula $V_{max}=K_{cat}[E]$, where [E] is the concentration of enzyme (mM), and Km (mM) is the Km in the FU fibrin assay. Activity is defined as the amount of TCA soluble product (expressed as mM of equivalent tyrosine released) per minute under reaction conditions.

Semi-alkaline protease activity at each concentration was measured by adding Suc-Ala-Ala-Pro-Phe-p-nitroanilide (100 µL of 0.5 mg/ml in $H_2O$), incubating the resultant solution for 1 hour at 37° C., and measuring the O.D. at 405 nm.

Figure 5:
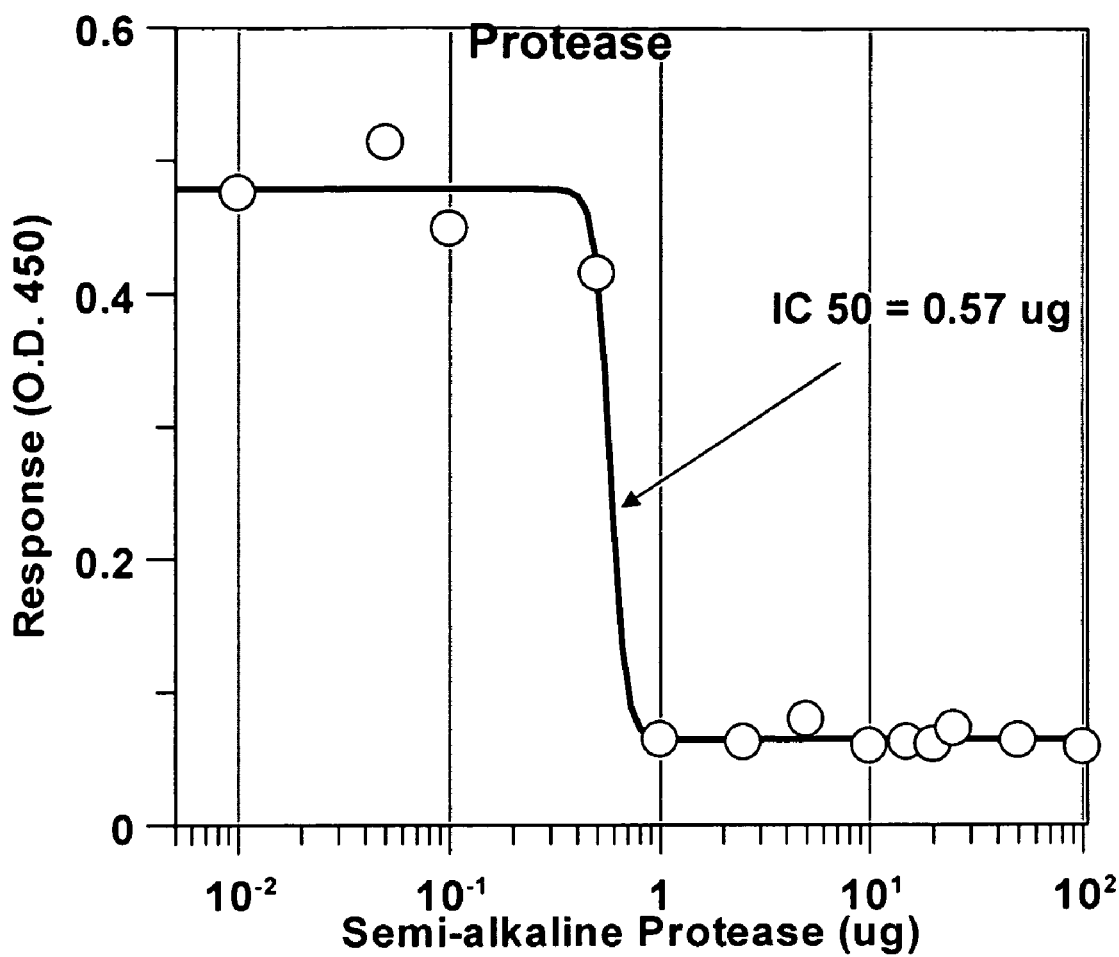
FIG. 5 charts the extent of PAI-1 inhibition as a function of the concentration of semi-alkaline protease in human serum.

PAI-1 activity was completely inhibited above a seaprose concentration of about 50 µg/mL, and was inhibited by 50% ($IC_{50}$) at a concentration of 0.56 µg/ml seaprose (FIG. 5).

EXAMPLE 2B

Inhibition of PAI-1 by Serapeptase

Serapeptase was isolated from aqueous extracts of commercially available serapeptase tablets (DASEN®, Takeda). The enzyme was incubated at various concentrations with 100 µL of human serum containing PAI-1 for 1 hour at 37° C. The PAI-1 activity was measured as described by Innovative Research (Human PAI-1 Activity Assay Kit) utilizing microtitre plates coated with urokinase and antibody to PAI-1.

Serapeptase activity was determined at each concentration by adding Azocasein (100 µL of 10 mg/ml in $H_2O$), incubating the resultant solution for 1 hour at 37° C. Then, an equal volume (200 µL) of 10% trichloroacetic acid (TCA) was added and the resultant solution was mixed and placed in ice for 10 minutes. Finally, the solution was centrifuged for 5 minutes at 8,500 RPM and the O.D. at 440 nm was measured.

Figure 6:
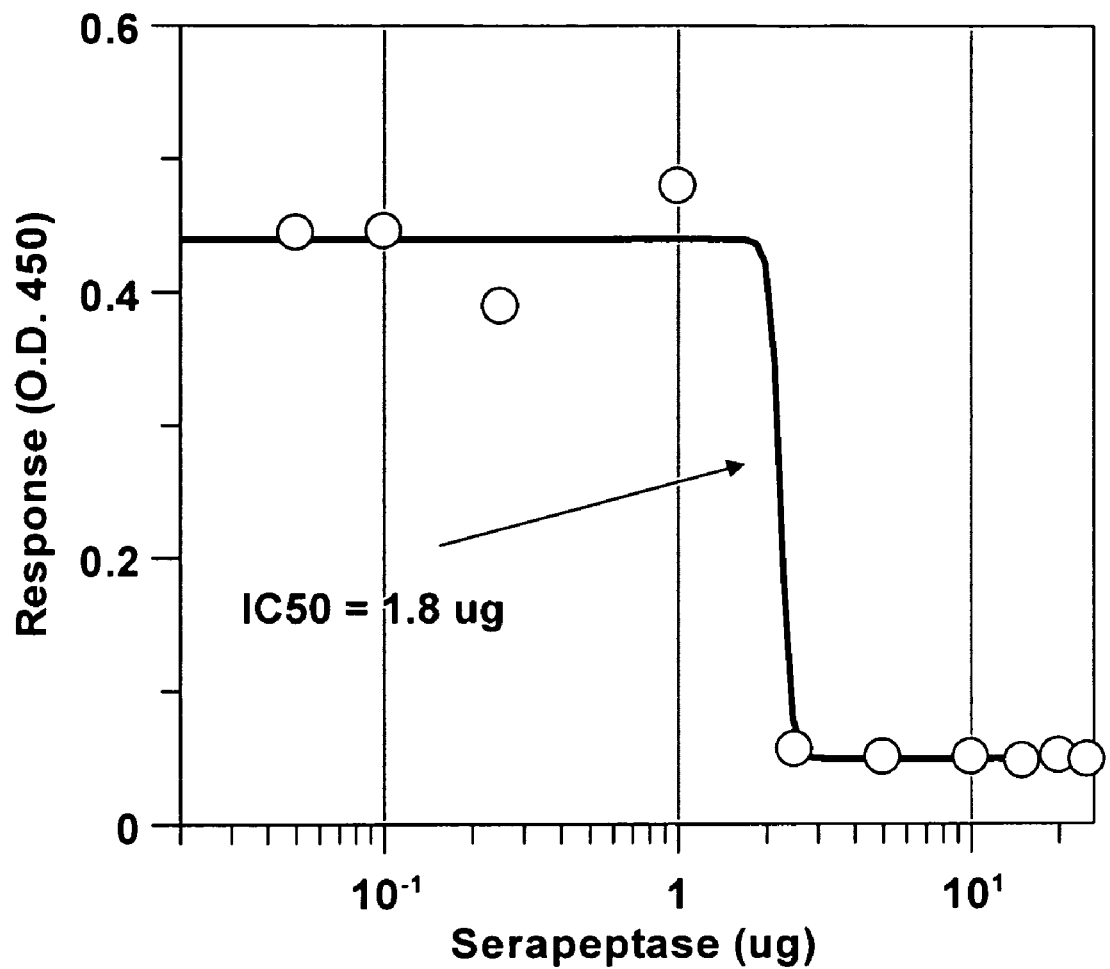
FIG. 6 charts the extent of PAI-1 inhibition as a function of the concentration of serapeptase in human serum.

PAI-1 activity was completely inhibited above a serapeptase concentration of about 20 µg/mL, and was inhibited by 50% ($IC_{50}$) at a concentration of 1.8 µg/ml serapeptase (FIG. 6).

EXAMPLE 2C

Inhibition of PAI-1 by Bromelain

Bromelain was obtained commercially from Amano Enzyme USA. The enzyme was incubated at various concentrations with 100 µL of human serum containing PAI-1 for 1 hour at 37° C. The PAI-1 activity was measured as described by Innovative Research (Human PAI-1 Activity Assay Kit) utilizing microtitre plates coated with urokinase and antibody to PAI-1.

Figure 7:
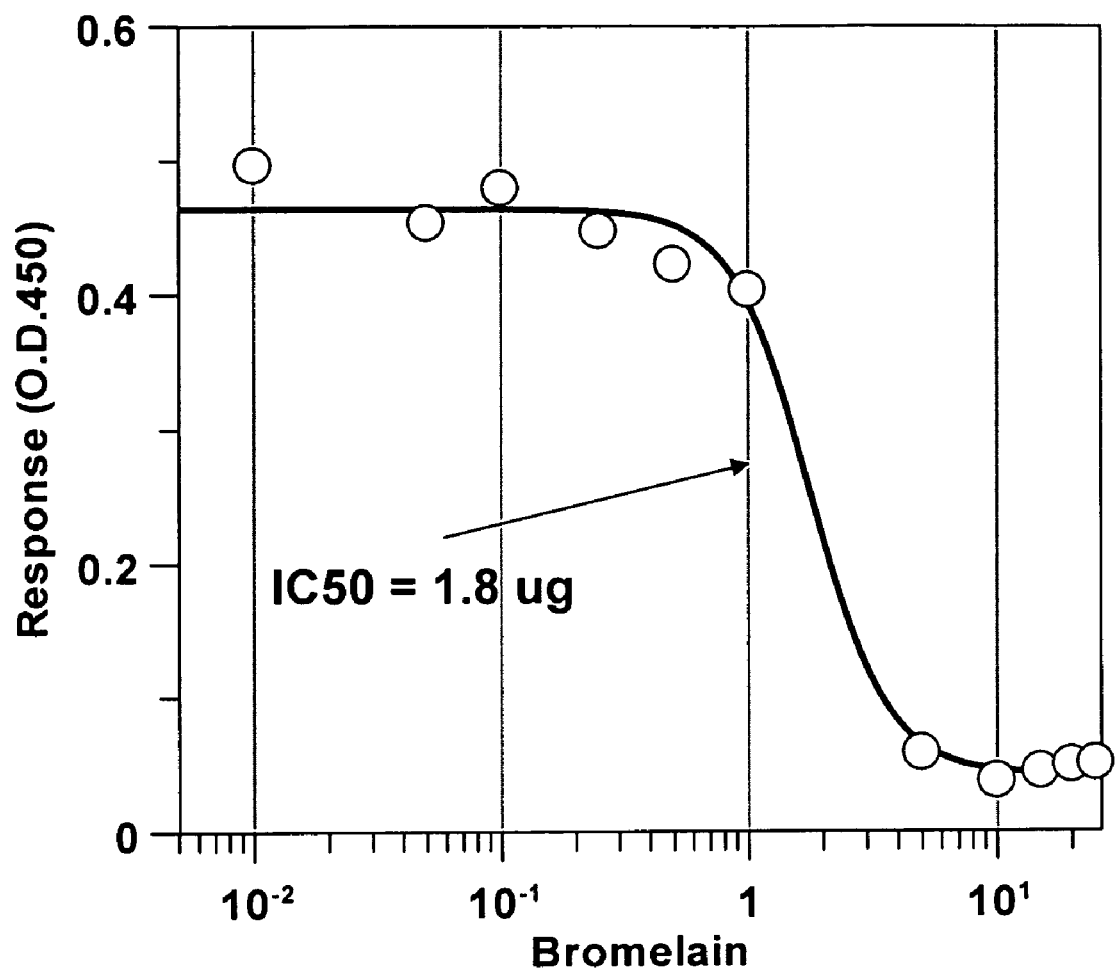
FIG. 7 charts the extent of PAI-1 inhibition as a function of the concentration of bromelain in human serum.

PAI-1 activity was completely inhibited above a bromelain concentration of about 25 µg/mL, and was inhibited by 50% ($IC_{50}$) at a concentration of 1.8 µg/ml bromelain (FIG. 7).

EXAMPLE 2D

Inhibition of PAI-1 by Pronase

Pronase was obtained commercially from Amano Enzyme. The enzyme was incubated at various concentrations with

TABLE 1

Summary of Enzyme Inhibition Studies

| ENZYME | Inhibition by AAT | Inhibition by ACT | Inhibition by MG | PAI-1 $IC_{50}$ (µg) | Specific Activity (FU/g) | Km Fibrinogen (mM) | Catalytic Efficiency ($K_{cat}$/Km) |
|---|---|---|---|---|---|---|---|
| Seaprose | − | − | + | 0.6 | 446,600 | 2.55 | 135,450 |
| Nattokinase | + | + | + | 22.8 | 14,170 | 4.31 | 11,470 |
| Bromelain | − | − | + | 1.8 | 10,830 | 2.53 | 4,550 |
| Papain | − | − | + | 6.3 | 3,260 | 1.06 | 497 |
| Serapeptase | − | − | + | 1.8 | 93,330 | 0.64 | 88,470 |

EXAMPLE 2A

Inhibition of PAI-1 by Seaprose

Semi-alkaline protease ("seaprose") was isolated from a fermentation of *Aspergillus melleus* (Amano Enzyme USA). The enzyme was incubated at various concentrations with 100 µL of human serum containing PAI-1 for 1 hour at 37° C. The PAI-1 activity was measured as described by Innovative Research (Human PAI-1 Activity Assay Kit) utilizing microtitre plates coated with urokinase and antibody to PAI-1.

100 μL of human serum containing PAI-1 for 1 hour at 37° C. The PAI-1 activity was measured as described by Innovative Research (Human PAI-1 Activity Assay Kit) utilizing microtitre plates coated with urokinase and antibody to PAI-1.

PAI-1 activity was completely inhibited above a pronase concentration of about 10 μg/mL, and was inhibited by 50% ($IC_{50}$) at a concentration of 0.9 μg/ml pronase (FIG. 8).

EXAMPLE 2E

Inhibition of PAI-1 by Papain

Papain was obtained commercially from Amano Enzyme, although it can be isolated from papaya latex by well known procedures in the art. The enzyme was incubated at various concentrations with 100 μL of human serum containing PAI-1 for 1 hour at 37° C. The PAI-1 activity was measured as described by Innovative Research (Human PAI-1 Activity Assay Kit) utilizing microtitre plates coated with urokinase and antibody to PAI-1.

PA-1 activity was completely inhibited above a papain concentration of about 10 μg/mL, and was inhibited by 50% ($IC_{50}$) at a concentration of 6.3 μg/ml Seaprose (FIG. 9).

COMPARATIVE EXAMPLE 1

Inhibition of PAI-1 by Nattokinase

The purpose of this comparative example was to demonstrate the significantly lower efficacy of nattokinase, as compared to the other enzymes described herein, to inhibit PAI-1 activity. Nattokinase can be isolated by extracting the enzyme from *Bacillus* natto fermented soy protein or is available commercially from Amano Enzyme USA. The enzyme was incubated at various concentrations with 100 μL of human serum containing PAI-1 for 1 hour at 37° C. The PAI-1 activity was measured as described by Innovative Research (Human PAI-1 Activity Assay Kit) utilizing microtitre plates coated with urokinase and antibody to PAI-1.

PAI-1 activity was completely inhibited above a nattokinase concentration of about 1000 μg/L and was inhibited by 50% ($IC_{50}$) at a concentration of 22.8 μg/ml nattokinase (FIG. 10), thus representing about a 20-100 fold decrease in efficacy as compared to the other enzymes described herein.

EXAMPLE 3

In vivo and Clinical Demonstrations of PAI-1 Inhibition

The purpose of this example was to demonstrate the in vivo effects of seaprose that are important in the treatment and prevention of cardiovascular diseases.

I. Mechanism of Action

The PAI-1 inhibitors are not inactivated by the serpin protease inhibitors normally found in human blood: $\alpha_1$-antitrypsin and $\alpha_1$-antichymotrypsin (Table 1). The PAI-1 inhibitors are bound by $\alpha_2$-macroglobulin, which is the most abundant protease inhibitor in human blood, in such a way as to inhibit protease activity with protein substrates but not peptidase activity with synthetic peptide substrates (FIG. 1 and Table 1).

A. Inhibition of Protease Activity by Macroglobulin

Separate portions of Seaprose (1 μg) were each incubated with $\alpha_2$-macroglobulin (0-250 μg) for 1 hour at 37° C. The resulting reaction mixtures were then assayed either for protease activity or peptidase activity. To evaluate protease activity, 100 μl of 10 mg/mL azocasein were added to the tube and incubated for 1 hour at 37° C. Then, 100 μL of 10% TCA were added, the tube mixed and centrifuged at 15,000 RPM for 5 minutes. The $O.D.^{440}$ of the supernatant was measured and taken as a measurement of protease activity (FIG. 1).

To evaluate peptidase activity, 1 μl of 5 mg/mL D-Val-Leu-Lys p-nitroanilide (Sigma Chemical Co.) was added to the other reaction mixture and incubated for 1 hour at 37° C. The $O.D.^{405}$ was measured and taken as a measurement of peptidase activity (FIG. 1).

Figure 2:
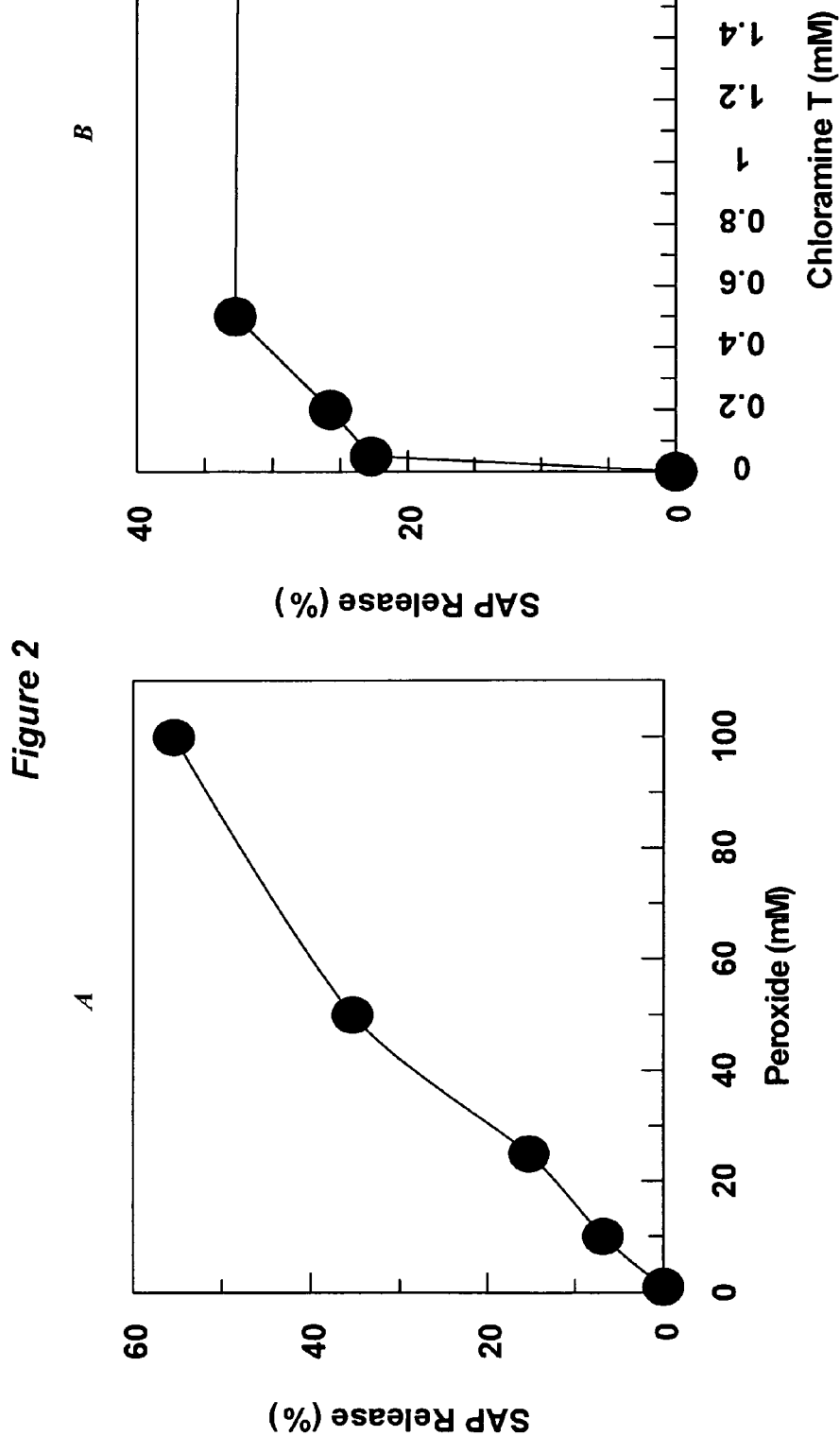
FIGS. 2A and 2B illustrate the release of Seaprose (SAP) from a Seaprose-$\alpha_2$-macroglobulin complex (SAP-MG) by the action of hydrogen peroxide (2A) or chloramine T (2B).

B. Effect of Hydrogen Peroxide and Chloramine T on the Release of Seaprose from Seaprose-$\alpha_2$-Macroglobulin Complex Presumably, small peptide substrates are able to penetrate within the "cage" structure of the $\alpha_2$-macroglobulin and are hydrolyzed by PAI-1 inhibitors while much larger protein substrates cannot penetrate the "cage" structure and do not come into contact with the PAI-1 inhibitors. While not wishing to be bound by any particular theory, the inventor suggests that the PAI-1 inhibitors are still active while sequestered inside the "cage" structure of $\alpha_2$-macroglobulin. The PAI-1 inhibitors can be released from the $\alpha_2$-macroglobulin "cage" structure by the action of reactive oxygen species such as those as generated by hydrogen peroxide or chloramine T in vitro (FIG. 2).

Thus, 1 μg Seaprose was incubated with 100 μg $\alpha_2$-macroglobulin for 1 hour at 37° C. Either peroxide (0-100 mM) or chloramine T (0-2 mM) were added and the reaction mixture was further incubated for 1 hour at 37° C. Released Seaprose was assayed using azocasein as described above. The released Seaprose was expressed as a percentage of the protease activity measured with no addition of $\alpha_2$-macroglobulin (FIG. 2).

Activated granulocytes that are present at sites of inflammation and thrombi are capable of releasing reactive oxygen species into the microenvironment at a level sufficient to release PAI-1 inhibitors from the complex with $\alpha_2$-macroglobulin (Stief, Thomas W. and Heimburger, Norbert Biol. Chem. 369 (1988) 1337-1342). This suggests a mechanism of action in which $\alpha_2$-macroglobulin functions as a carrier protein for the PAI-1 inhibitors and transports them to the site of inflammation or thrombi where the PAI-1 inhibitors are released by the action of activated granulocytes. The released PAI-1 inhibitors are then free to inactivate PAI-1 that is present at the site of inflammation or thrombi and thereby increase the local concentration of plasmin leading to the degradation of cross-linked fibrin. In addition, because the PAI-1 inhibitors also exhibit direct protease activity with cross-linked fibrin substrate in vitro (Table 1), the PAI-1 inhibitors also can directly degrade cross-linked fibrin at the site of inflammation or thrombus.

In contrast to the enzymes described hereinabove, another known PAI-1 inhibitor, namely nattokinase, is inactivated by the protease inhibitors $\alpha_1$-antitrypsin and $\alpha_1$-antichymotrypsin. Nattokinase also is relatively less effective as a PAI-1 inhibitor and as a protease capable of degrading cross-linked fibrin (Table 1).

In this example, further studies focused on the PAI-1 inhibitor seaprose because this enzyme exhibits a higher level of PAI-1 inhibition activity as well as cross-linked fibrin activity (Table 1).

C. In vivo Evidence for Fibrinolytic Activity

This study was conducted at Nanotherapeutics, Inc., Gainesville, Fla. under an IACUC (Institutional Animal Care and Use Committee) approved protocol.

The right hand jugular vein in each of 6 rats was exposed surgically and an initial blood flow reading was recorded.

Blood flow was measured by a T206 Transonic Blood Flow Meter fitted with probe 2SB. A thrombus was then introduced chemically in the right hand jugular vein (the left vein served as a control) and the incision was closed. After two hours the right hand vein was again surgically exposed and blood flow through the right hand vein was measured and observed to be essentially blocked.

Figure 3:
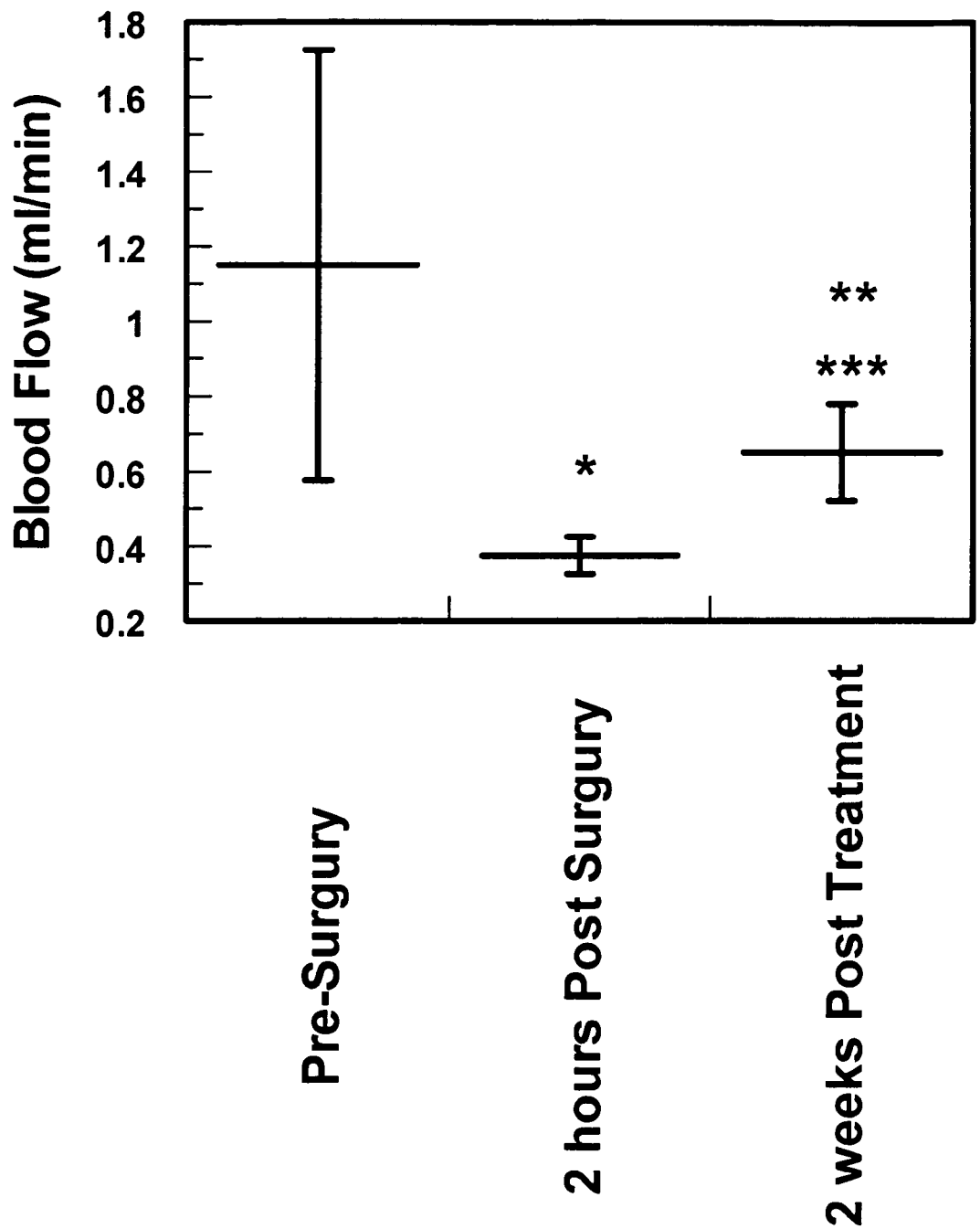
FIG. 3 illustrates the restorative effect of Seaprose in rats on the blood flow in veins that were blocked with thrombi.
Figure 4:
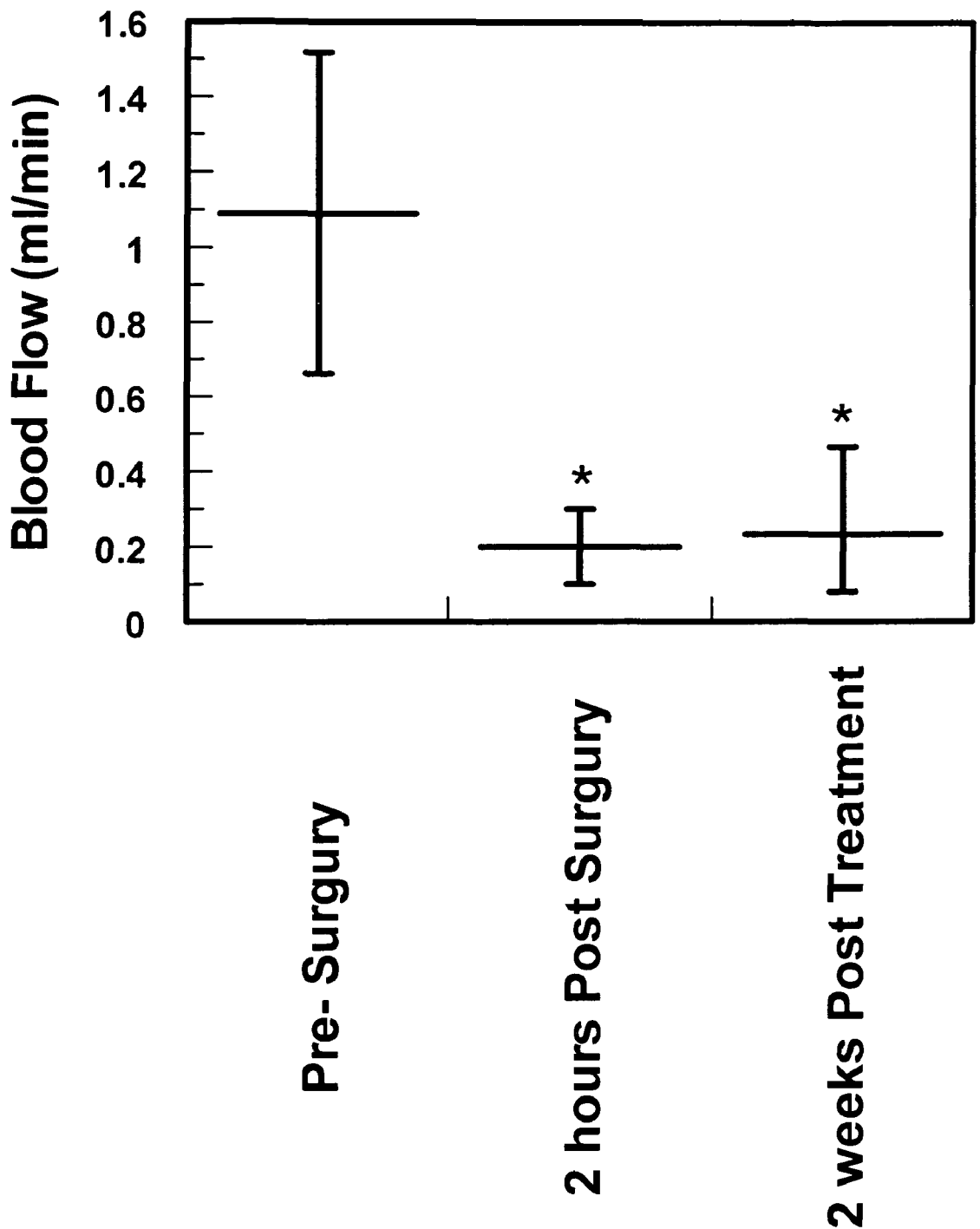
FIG. 4 illustrates the effect of the absence of Seaprose in control rats on the blood flow in blood veins that were blocked with thrombi.

One half of the rats were then fed Seaprose in their diet (50 mg/kg/day) for two weeks after which the right hand vein was surgically exposed and the blood flow was found to be restored to levels before thrombus induction (FIG. 3). The other half of the rats (control rats) were not fed Seaprose and there was no restoration of blood flow in these rats after two weeks (FIG. 4). Visual examination of the veins showed no sign of thrombus in rats fed Seaprose after two weeks while control rats showed the presence of a thrombus.

D. Clinical Evidence for PAI-1 Inhibition.

The clinical study described below was conducted at the AMK Clinical Laboratory, Gainesville, Fla. with IRB (Institutional Review Board) approval. Three subjects with high PAI-1 levels were selected for the study. The subjects were not on medications. An initial blood sample was taken one week before starting the study (Pre-SAP). For a period of 4 weeks the subjects took one 15 mg capsule of Seaprose after breakfast and one 15 mg capsule of Seaprose after dinner. A blood sample was taken once a week at (SAP). Two weeks after completing the Seaprose treatment an additional blood sample was taken at (Post SAP). The PAI-1 level was determined by ELISA (Innovative Research, Inc.), the PAP level was determined by ELISA (ALPCO Diagnostics), the D-Dimer level was determined by ELISA (American Diagnostica, Inc.) and the LDL level was determined by standard methods (Quest Diagnostics). The normal level for each test was determined by the vendor of the assay. The ELISA data was determined in triplicate with the average reported with a variation less than 5%. Values for the SAP results were an average of the 4 blood samples with variation less than 10%. The results of the clinical study are presented in Table 2.

TABLE 2

Clinical Results for the Treatment of Humans with Seaprose

| Subject | Treatment | PAI-1 (U/ml) | PAP (µg/mL) | D-Dimer (ng/ml) | D-Dimer Low Value (week) | LDL (mg/dl) |
|---|---|---|---|---|---|---|
| 1 | Pre-SAP | 79 | 130 | 502 | | 192 |
| | SAP | 8.8 | 220 | 377 | 263 (4) | 148 |
| | Post SAP | 16.2 | 214 | 337 | | 155 |
| 2 | Pre-SAP | 16.2 | 263 | 567 | | 168 |
| | SAP | 7.7 | 256 | 476 | 433 (3) | 133 |
| | Post SAP | 9.4 | 289 | 539 | | 161 |
| 3 | Pre-SAP | 29.1 | 223 | 585 | | 114 |
| | SAP | 5.6 | 319 | 573 | 476 (3) | 100 |
| | Post SAP | 11.7 | 412 | 567 | | 98 |
| Normal | | 12.8 | 290 | <400 | <400 | <130 |

Thus, the blood samples were tested for PAI-1 activity, PAP level (plasmin in the blood exists as a Plasmin-AntiPlasmin complex), D-Dimer level (D-Dimers are the final degredation product of cross-linked fibrin and high D-Dimer levels are an indication of an ongoing inflammation or thrombus), and low density lipids (LDL).

Subject 1 had a very high level of PAI-1 (79 U/mL) that was reduced during Seaprose treatment to levels within the normal range (8.8 U/mL). When Seaprose treatment was stopped for two weeks the level of PAI-1 activity returned to above normal (16.2 U/mL). During Seaprose treatment the low initial level of plasmin (130 µg/mL) present in the blood increased to near normal levels (220 µg/mL) and fell slightly after Seaprose treatment (214 µg/mL). The D-Dimer level initially was high (502 ng/mL) but fell to normal levels during Seaprose treatment (average of 377 and a low of 263 ng/mL at week 4 of treatment). The LDL levels initially were very high (192 mg/dL) but were reduced to near normal levels (148 mg/dL) during Seaprose treatment. The LDL again rose after Seaprose treatment (155 mg/dL). These results indicate that Seaprose was effective in inhibiting PAI-1 and that the level of plasmin increased as a result of the PAI-1 inhibition, which resulted in an improvement in cardiovascular health as measured by a dramatic lowering of the D-Dimer concentration. There was also a dramatic lowering of the LDL level indicating that Seaprose activated $\alpha_2$-macroglobulin (see Degryse, Bernard, et. al. *The Journal of Biological Chemistry* 279(21) (2004) 22595-22604, Wu, Sean M. et. al. *The Journal of Biological Chemistry* 272(33) (1997) 20627-20635). HDL was unchanged during the study.

Subject 2 exhibited slightly high PAI-1 activity (16.2 U/mL) which decreased to a normal level (7.7 U/mL) upon Seaprose treatment and rose slightly (9.4 U/mL) after Seaprose treatment was stopped. Plasmin levels were in the normal range at all times. D-Dimer levels were high initially (567 ng/mL) and decreased during Seaprose treatment with a low point at week 3 (433 ng/mL) which reached normal levels. D-Dimer concentration increased to high levels (539 ng/mL) after Seaprose treatment was stopped. LDL levels decreased from an above normal level (168 mg/dL) to a normal level (133 mg/mL) while undergoing Seaprose treatment and then rose significantly (161 mg/dL) after Seaprose treatment was stopped. HDL was unchanged during the study. These results with Subject 2 indicate that Seaprose did lower PAI-1 activity during treatment resulting in a lower D-Dimer level. There was a dramatic lowering of LDL during Seaprose treatment.

Subject 3 had elevated PAI-1 activity (29.1 U/mL) which decreased to normal levels (5.6 U/mL) during Seaprose treatment and increased again post Seaprose treatment (11.7 U/ml). The plasmin levels also increased from below normal levels (223 µg/mL) to above normal levels during Seaprose treatment (319 µg/mL) and after Seaprose treatment (412 µg/mL). The D-Dimer level was initially above normal (585 ng/mL) but decreased to normal levels during Seaprose treatment (476 ng/mL during week 3) and rose during post Seaprose treatment (567 ng/mL). LDL levels were in the normal range initially (114 mg/dL) and decreased slightly during Seaprose treatment (100 mg/dL). The results from Subject 3 again indicate that Seaprose inhibits PAI-1 activity which then lowers the D-Dimer level (cardiovascular risk) by elevating the plasmin level.

All publicly available documents, including U.S. patents, cited herein are incorporated by reference in their entireties as if fully set forth herein.

Various substitutions and modifications may be made to the invention disclosed herein without departing from the scope and spirit of the invention. The foregoing description and examples are illustrative only, and do not limit the scope of the invention, which is defined by the claims.

What is claimed is:

1. A method of inhibiting plasminogen activator inhibitor type 1 (PAI-1) activity in a subject in need thereof having a greater than normal blood level of PAI-1 activity, comprising orally administering to the subject an effective amount of at least one enzyme selected from the group consisting of semi-alkaline protease, bromelain, serapeptase, pronase, and papain.

2. The method according to claim 1, wherein the enzyme is pronase.

3. The method according to claim 1, wherein the enzyme is papain.

4. The method according to claim 1, where the enzyme is semi-alkaline protease.

5. The method according to claim 1, where the enzyme is bromelain.

6. The method according to claim 1, wherein the enzyme is serapeptase.

7. The method according to claim 1, wherein the subject presents with at least one risk factor selected from the group consisting of obesity, diabetes, high blood pressure, stress, lowered estrogen levels, chronic inflammation, and combinations thereof.

8. The method according to claim 1, wherein the subject has a blood level of PAI-1 activity of greater than 12.8 U/ml.

* * * * *